US008770040B2

(12) United States Patent
Boschi et al.

(10) Patent No.: US 8,770,040 B2
(45) Date of Patent: Jul. 8, 2014

(54) APPARATUS AND METHOD FOR MEASURING THE FLOW-RATE OF A MULTIPHASE FLUID STREAM

(75) Inventors: Stefano Boschi, Gorgonzola (IT); Paolo Andreussi, Pisa (IT)

(73) Assignees: ENI S.p.A., Rome (IT); Tea Sistemi S.p.A., Pisa (IT)

( * ) Notice: Subject to any disclaimer, the term of this patent is extended or adjusted under 35 U.S.C. 154(b) by 224 days.

(21) Appl. No.: 13/499,054

(22) PCT Filed: Sep. 21, 2010

(86) PCT No.: PCT/IB2010/002371
§ 371 (c)(1),
(2), (4) Date: Jun. 5, 2012

(87) PCT Pub. No.: WO2011/039593
PCT Pub. Date: Apr. 7, 2011

(65) Prior Publication Data
US 2012/0234103 A1    Sep. 20, 2012

(30) Foreign Application Priority Data
Sep. 29, 2009   (IT) .............................. MI2009A1671

(51) Int. Cl.
*G01F 1/74*     (2006.01)
(52) U.S. Cl.
USPC ...................................................... 73/861.04
(58) Field of Classification Search
USPC ...................................................... 73/861.04
See application file for complete search history.

(56) References Cited

U.S. PATENT DOCUMENTS

| | | | |
|---|---|---|---|
| 5,591,922 A * | 1/1997 | Segeral et al. | 73/861.04 |
| 6,546,809 B1 | 4/2003 | Andreussi | |
| 7,474,969 B2 * | 1/2009 | Poulisse | 702/45 |
| 7,717,000 B2 * | 5/2010 | Xie et al. | 73/863.03 |
| 7,942,065 B2 * | 5/2011 | Xie | 73/861.04 |
| 8,521,450 B2 * | 8/2013 | Oddie | 702/47 |
| 2009/0223309 A1 | 9/2009 | Kurz | |
| 2010/0145634 A1 | 6/2010 | Pinguet et al. | |

FOREIGN PATENT DOCUMENTS

| | | |
|---|---|---|
| DE | 197 06 949 | 8/1998 |
| GB | 2 447 908 | 10/2008 |
| WO | 00 49370 | 8/2000 |
| WO | 2007 002190 | 1/2007 |

OTHER PUBLICATIONS

International Search Report Issued Jan. 28, 2011 in PCT/IB10/02371 Filed Sep. 21, 2010.

* cited by examiner

*Primary Examiner* — Jewel V Thompson
(74) *Attorney, Agent, or Firm* — Oblon, Spivak, McClelland, Maier & Neustadt, L.L.P.

(57) ABSTRACT

An apparatus for measuring a multiphase fluid stream which flows in a pipe (2) comprising: a measuring unit (11), coaxial to the pipe, consisting of an isokinetic sampling device (1) suitably configured for allowing the equidistribution of the flow at the inlet in n channels (6) having an area A, of which m are sampling channels and a flow restriction (13) both equipped with differential pressure measuring means (12, 14), a phase separator (15), connected to the sampling device, measurers and regulation means downstream of said separator. A method in accordance with said apparatus which comprises: the isokinetic sampling of a portion q of the multiphase flow Q at the inlet, measuring the flow-rates of the liquid qL and gas qG of the portion sampled and calculating the liquid and gas flow-rates (QL and Q0) from the sampling sections according to the equations QG=n/tn qG and QL=n/m qL. The method provides isokinetic sampling for portions of flow removed ranging from 5% to 20%.

19 Claims, 4 Drawing Sheets

APPARATUS AND METHOD FOR MEASURING THE FLOW-RATE OF A MULTIPHASE FLUID STREAM

The present invention relates to an apparatus and method for measuring the flow-rate of a multiphase flow, by the isokinetic sampling of a significant portion (5-20%) with respect to the overall flow-rate. The present invention is particularly, but not exclusively, suitable for measuring multiphase flows in the oil industry.

During the production of oil and gas, measurements are taken in a pipe which transports hydrocarbons, for determining the flow of the multiphase stream and single phases, the multiphase flow consisting of a biphasic or triphasic combination of oil-water-gas. The flow measurements of the different phases in a pipe transporting oil/hydrocarbons are often useful for controlling and regulating the production of hydrocarbons and for evaluating the water and gas content inside the multiphase flow.

In order to accurately measure the flow of the different phases of the multiphase oil-water-gas stream, it is necessary to have multiphase measurers (MPFM) capable of operating in the different flow regimes.

A certain number of different multiphase flow measurers have mainly been developed for applications in the oil industry, some based on the use of ionizing radiations, others based on the use of microwaves. These instruments are characterized by strong measurement uncertainties. The errors become significant when these measurement instruments are used for flow-rate measurements on multiphase streams characterized by a high gas fraction (GVF>98%).

Measuring devices using a γ-ray source for determining the density of the mixture, such as those indicated in U.S. Pat. No. 4,289,02, U.S. Pat. No. 5,101,163 U.S. Pat. No. 5,259,239 and WO 2007/034132, together with a low accuracy, have the limitation of having a high cost, are difficult to install in production plants and are potentially dangerous for the health, safety and environment. Furthermore, if the vapour phase is widely prevalent, the measurement of the density of the mixture by means of a γ-ray densitometer is relatively inaccurate.

The problems encountered in applying multiphase flow measurers to the case of a high GVF have led to the development of a multiphase measurer, based on the principle of isokinetic sampling, disclosed in International patent application WO 2000/49370. This measurer is capable of removing fractions representative of the multiphase flow (5%÷20% of the total capacity) by suitable adjustments of the flow-rates removed and accurately measuring the gas and liquid flow-rates of the multiphase stream at the inlet. The measuring device however suffers from possible inefficiency linked to the operating self-calibration method.

Other devices, such as those disclosed in International patent applications WO 2005/031311 and WO 2007/060386, use isokinetic sampling coupled with a total flow-rate measurer of the multiphase stream regardless of the isokinetic sampling, allowing the liquid and gas flow-rates of the multiphase mixture to be characterized.

All of the devices mentioned above, based on isokinetic removal and sampling, have limits associated with the sampling probe. Both single-gate and multiple-gate sampling probes function correctly in the presence of a continuous gaseous phase containing dispersed droplets, but are less effective in the case of high liquid fractions.

The objective of the present invention, better described in the enclosed claims, is to provide an apparatus and simple method for measuring a multiphase flow, capable of operating with high volumetric liquid fractions (LVF) >10%, whatever the flow regime may be (for example laminar, bubble, slug).

The measuring apparatus according to the present invention has a sampling section with a geometry which is such as to guarantee the equidistribution of the total gas and liquid flow-rate inside a certain number n of channels, of which m are sampling, and the remaining non-sampling channels.

According to an important aspect of the present invention, the sampling section comprises an isokinetic sampling device for the sampling of a portion of the multiphase stream, suitable for separating the multiphase stream into a sampled fraction and a non-sampled fraction, consisting of a tubular body and a distributing body situated inside the tubular body and suitable for generating a uniform radial distribution of the flow of the multiphase stream entering into n channels, of which m are sampling channels, annularly arranged on the distributing body which guarantee for the sampled stream, fractions by volume of the phases present and rates almost identical to those of the non-sampled stream.

According to another important aspect of the invention, the tubular body is composed of two truncated-conical sections, one divergent and one convergent, axially connected to each other by a cylindrical section and the distribution body comprises an annular support, fixed inside the cylindrical section of the tubular body, and a rotation solid positioned coaxially inside the annular support and comprising two substantially conical ogives extending axially and symmetrically above and below the annular support, respectively inside the upper half of the cylindrical section and the divergent section and inside the lower half of the cylindrical section and the convergent section of the tubular body. Said rotation solid is substantially obtained by the rotation of a semi-ellipse around the cutting line.

According to a further aspect of the invention, the channels situated along the annular support are equidistanced angularly and equidistributed and have an equal section. Furthermore, each channel comprises a first section parallel to the axis of the annular body, coinciding with the flow direction, and a second section which, in the case of non-sampling channels is tilted towards the inside of the tubular body, to convey the non-sampled fraction of the multiphase stream into the same, whereas in the case of sampling channels, it is tilted towards the outside, to convey the sampled fraction towards a gas-liquid separation unit.

Under these conditions, if $A_1$ represents the area of the flow section of the total flow and $A_2$ represents the overall area of the flow section of the sampled flow, the sampling can be defined as isokinetic if the ratio between the overall flow-rate q sampled in the section $A_2$ and the total flow-rate Q which flows towards the section $A_1$ is equal to the ratio $A_2/A_1$. It should be noted that in the sampling section proposed, by compelling the flow at the inlet to be equally subdivided inside a number n of channels each having an area A, of which m are sampling channels, this gives:

$$A_1 = A \cdot n \tag{1}$$

$$A_2 = A \cdot m \tag{2}$$

By dividing (2) with (1) member by member, the following is obtained:

$$\frac{m}{n} = \frac{A_2}{A_1} \tag{3}$$

Consequently, in the case of isokinetic sampling using the apparatus object of the present invention, if $q_L$ and $q_G$ are respectively the flow-rates of liquid and gas measured in the portion sampled and $Q_L$ and $Q_G$ are respectively total flow-rates of liquid and gas which are flowing in the pipe, the following relations are valid:

$$Q_L = \frac{A_1}{A_2} q_L = \frac{n}{m} q_L \qquad (4)$$

$$Q_G = \frac{A_1}{A_2} q_G = \frac{n}{m} q_G \qquad (5)$$

$Q_L$ and $Q_G$ can be obtained directly from $q_L$ and $q_G$ measured after sampling and separation on the basis of the relations (4) and (5). The sampled flow-rates of liquid and gas $q_L$ and $q_G$ are measured using measurers of the known type for single-phase streams. The flow-rate of the multiphase stream at the inlet is the sum of the liquid and gas flow-rates $Q_L$ and $Q_G$ calculated.

According to another aspect of the present invention, a method is provided for measuring the liquid and gaseous flow-rates of a multiphase stream wherein, for the sampling of the portion of the multiphase stream, the latter is divided, according to a uniform radial distribution of the flow, into n streams, of which m are sampling streams having rates and volumetric fractions of the phases present almost identical to those of the non-sampled streams, said distribution of the flow being effected in n channels annularly arranged, wherein the m sampling channels have an overall passage section equal to $A_2$. A differential pressure signal is therefore obtained downstream of the sampling between the sampled fraction and non-sampled fraction and the flow-rate of the sampled portion of the overall stream is varied so that said differential pressure signal is equal to zero. Under the isokinetic conditions thus obtained, the total flow-rate of the multiphase stream is calculated as the sum of the flow-rates of the gaseous fraction $Q_G$ and the liquid fraction $Q_L$ once the flow-rates of the gas phase $q_G$ and liquid phase $q_L$ in the sampled portion of the overall stream have been measured, on the basis of the relations $$Q_G = A_1/A_2 q_G = n/m q_G$$

and $$Q_L = A_1/A_2 q_L = n/m q_L.$$

Further characteristics and advantages of the apparatus and method for measuring the flow-rate of a multiphase flow according to the present invention will appear more evident from the following description of one of its embodiments, for illustrative and non-limiting purposes, with reference to the enclosed drawings, in which.

Figure 1:
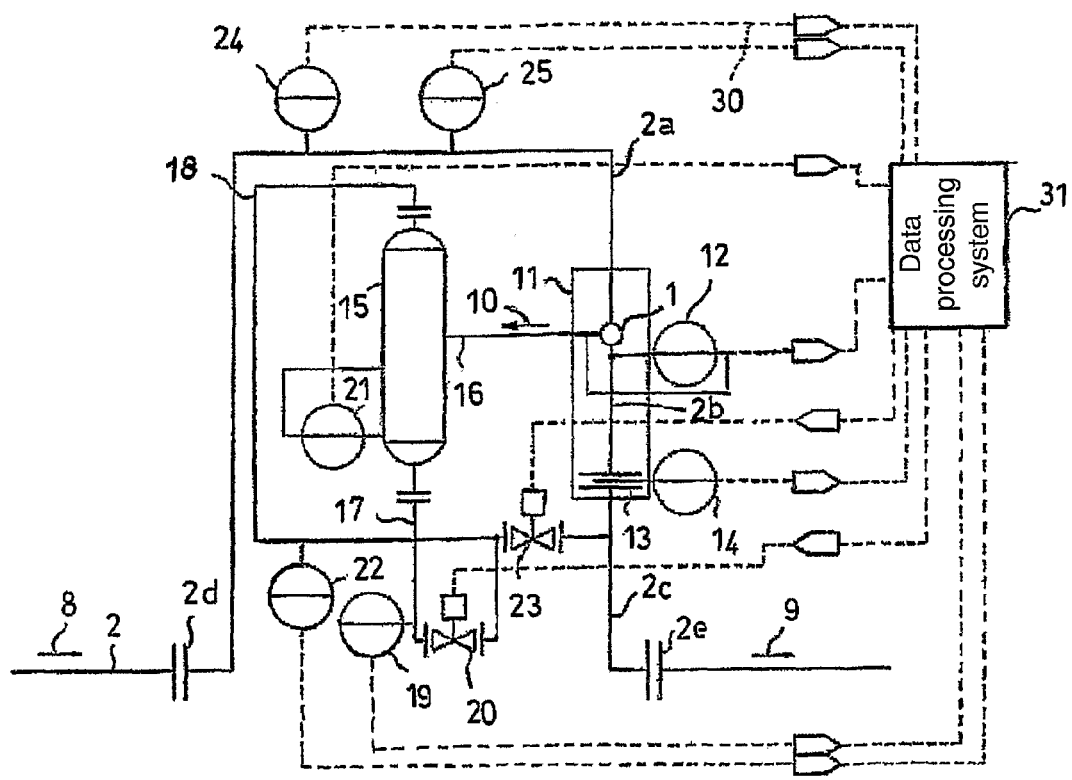
FIG. 1 shows the functional diagram of an apparatus for measuring the flow-rate of a multiphase flow, according to the present invention.

With reference to FIG. 1, the apparatus according to the present invention for measuring the flow-rate of a multiphase flow 8 which flows inside a pipe 2 comprises a measuring unit 11 situated between two vertical portions 2a, 2c of the pipe 2, in which the flow flows downwards, and included between two flanged sections 2d and 2e of the pipe 2.

Figure 2:
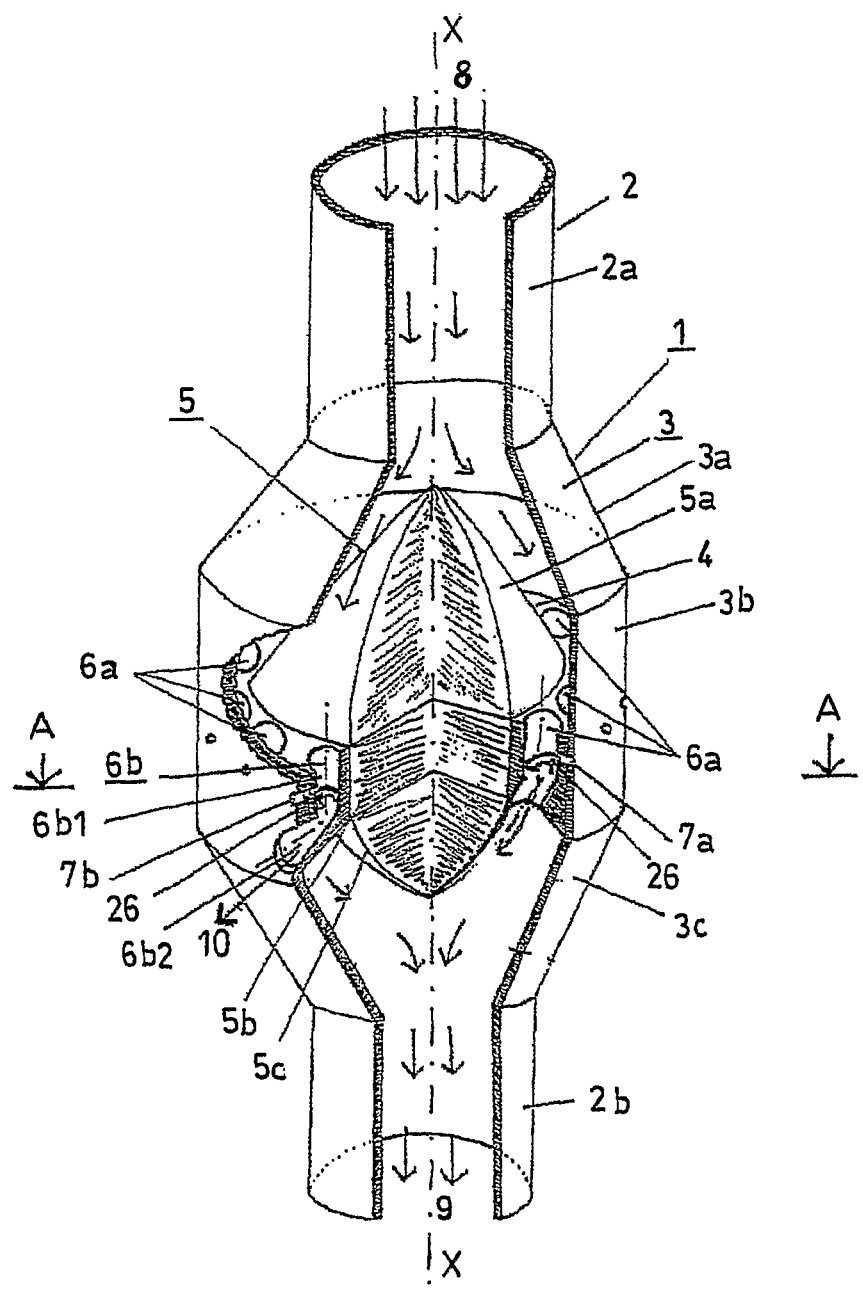
FIG. 2 represents a partially sectional perspective view of the isokinetic sampling section of the measuring apparatus of FIG. 1.

The measuring unit 11 comprises an isokinetic sampling device 1, described in greater detail hereunder with reference to FIG. 2, whose function is to remove a flow-rate q from the multiphase flow deviating a part 10 of the total flow-rate Q of the multiphase flow 8 at the inlet of the pipe 2, inside a gas-liquid separator 15, of the known type. A differential pressure measuring device 12, of the known type, is situated in correspondence with the isokinetic sampling device 1 for measuring the pressure difference after the sampling between the fluid removed and the non-removed fluid; in order for the sampling to be isokinetic, the pressure difference must be zero.

The measuring unit 11 also contains, downstream of the isokinetic sampling device 1, interspersed by the section of vertical pipe 2b, a flow restriction 13, which is such as to create the pressure drop necessary for effecting the sampling in the device 1 situated upstream. A differential pressure measuring device 14, of the known type, can be situated in correspondence with the flow restriction 13, to measure the pressure drop due to the passage of the flow through the flow restriction 13.

The isokinetic sampling device 1 is in communication with the gas-liquid separator 15, to which the portion of sampled multiphase flow 10 is fed by means of a horizontal section of pipe 16, to be separated into its liquid and gaseous components. The liquid phase leaves the bottom of the separator 15 through a pipe 17, whereas the gaseous phase leaves the upper end of the separator 15 through a pipe 18.

The pipe 17, which is configured so as to feed the liquid portion inside the pipe of the gaseous phase 18, before its insertion in the section of pipe 2c downstream of the unit 11, is intersected by a measuring device of the liquid flow-rate 19, of the known type, and downstream of a valve 20, which can be closed to effect measurements discontinuously, as better described hereunder. A level indicator 21 is associated with the separator 15, equipped with a differential level indicator.

The pipe 18 is intersected, upstream of the insertion of the pipe 17, by a measuring device of the gas flow-rate 22, of the known type, and, downstream, by a regulation valve 23 of the flow-rate of sampled fluid 10.

Furthermore, upstream of the measuring unit 11, an absolute pressure indicator 24 and a temperature indicator 25 are associated with the pipe 2, for monitoring the pressure P and temperature respectively of the multiphase fluid which is flowing inside the pipe 2.

The dashed lines 30 represent the electric connections of the valves and measuring devices to a data processing system 31. In particular, during the operative conditions, the system is configured to receive and process the signal transmitted by the instruments and send operative signals to the valves according to what is indicated in the description of the method relating to the measuring apparatus.

With reference to FIG. 2, the isokinetic sampling device 1 comprises a tubular body 3, consisting of a divergent section 3a, a cylindrical section 3b and a convergent section 3c, coaxially connected with each other in sequence.

In particular, the divergent section 3a of the tubular body 3 extends between the upper section of pipe 2a and the cylindrical section 3b and has a truncated-conical form with a smaller diameter equal to the diameter of the upper section of piping 2a and a larger diameter equal to the diameter of the section of piping 3b. The convergent section 3c of the tubular body 3 extends between the cylindrical section 3b and the lower section of piping 2b and has a truncated-conical form with a larger diameter equal to the diameter of the tubular section 3b and a smaller diameter equal to the diameter of the lower section of piping 2b.

Inside the tubular body 3, in correspondence with the lower half of the cylindrical section 3b, an annular support 4 is axially fixed for a rotation solid indicated as a whole with 5 and comprising two substantially conical ogives 5a and 5b extending axially above and below the annular support 4 respectively inside the upper half of the cylindrical section 3b and the divergent section 3a and inside the lower half of the cylindrical section 3b and convergent section 3c of the tubular body 3.

The first ogive 5a is positioned with the tip facing upwards and the circular base resting on the annular support 4, whereas, second ogive 5c is positioned with the tip facing downwards and the circular base resting on the annular support 4.

n channels 6a, b, pass through the annular support 4, each having a crossing section A, angularly equidistanced, of which n−m are non-sampling channels 6a and m are sampling channels 6b.

The sampling channels 6b are pass-through for the annular support 4, for a first section 6b1 parallel to the axis of the tubular body 3 and for a second section 6b2 tilted towards the outside to allow the conveying of the fluids collected towards the separator 15. The non-sampling channels 6a are pass-through for the annular support 4, for a first section 6a1 parallel to the axis and for a second section 6a2 tilted towards the inside by an angle equal to that of the sampling channels to convey the fluids not collected towards the inside of the convergent section 3c.

Figure 3:
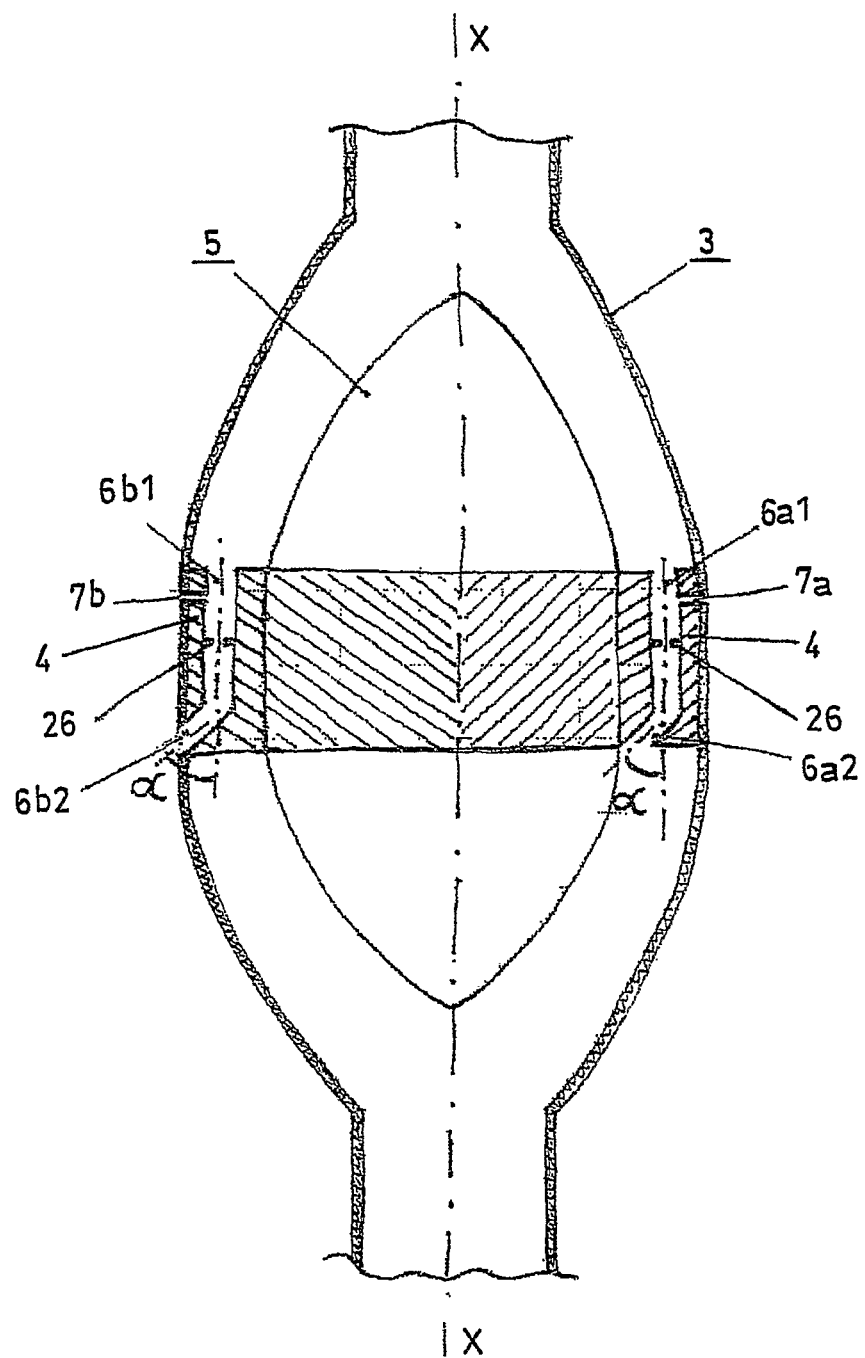
FIG. 3 is an axial section of the sampling device of the apparatus of FIG. 1 produced with a plane containing the axis X-X of FIG. 2.

With reference to FIG. 3, D being the diameter of n channels in which the multiphase fluid is distributed, each channel is characterized by a length l of the vertical section before the curvature equal to 8 to 10 times the diameter D and an inclination angle α ranging from 10 to 30°. At a distance d of a few mm and 2D from the upper base of the annular support 4 on the cylindrical section 3b, there is a pressure measuring point 7a,b which puts each channel 6a,b in communication with the outside. In particular, the pressure measuring points 7b of the sampling channels 6b are connected to each other in a conventional manner, as also the pressure measuring points 7a of the non-sampling channels 6a. The differential pressure measuring device 12 is inserted between the pressure measuring points 7b of the sampling channels 6b and the pressure measuring points 7a of the non-sampling channels 6a.

In each channel, either sampling 6b or non-sampling 6a, downstream of the pressure measuring points 7a, and 7b, at a height h from the upper base of the annular support 4 equal to four to five times the diameter D, there is a flow restriction 26 which reduces the passage section A by 20-30%. The main effect of this narrowing inside the channels is to counterbalance the distortion effect of the fluid threads in correspondence with the pressure measuring points, due to the different inclination of the final section.

Figure 4:
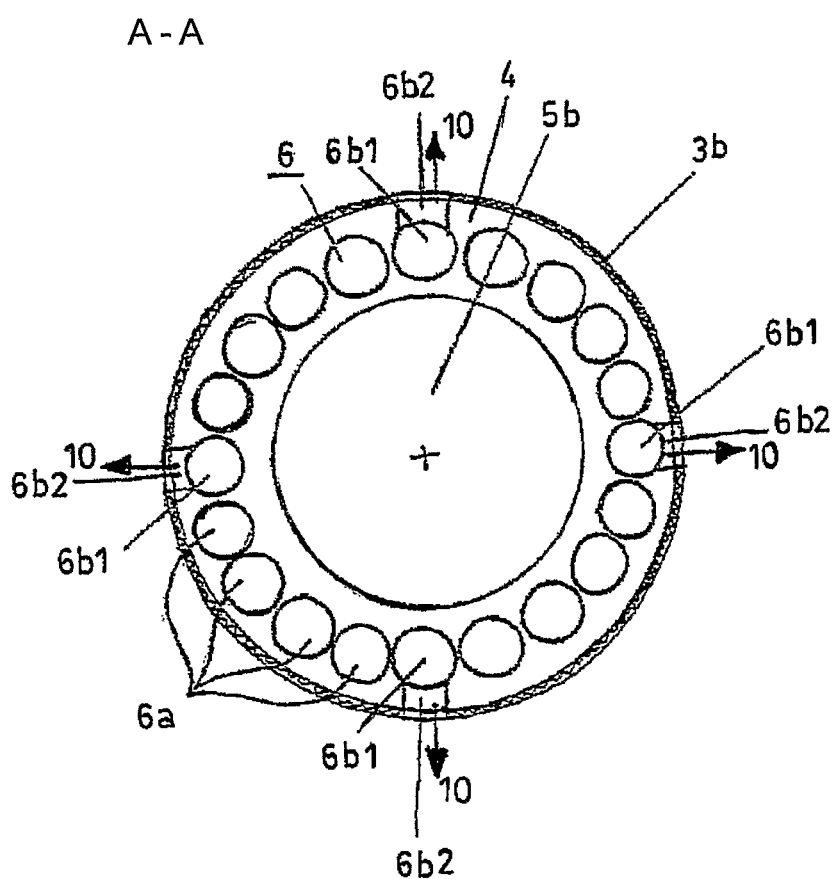
FIG. 4 shows a transversal section of the sampling device according to the arrows A-A of FIG. 2.

With reference to FIG. 4, this shows the section A-A orthogonal to the vertical axis of FIG. 2, relating to a specific configuration of the apparatus, object of the present invention, characterized by a distribution of n=20 total channels of which n−m=16 non-sampling 6a and m=4 sampling 6b, the latter being angularly equi-distributed with respect to the total on the section of the annular support 4. In particular, FIG. 4 shows the two sections 6b1 and 6b2 of n=4 sampling channels 6b.

The operating procedure for effecting the continuous measurement of the multiphase flow stream, relating to the measuring apparatus, object of the present invention, is illustrated hereunder.

Under the operating conditions, with reference to FIG. 2 and FIG. 3, the multiphase flow 8, which is flowing inside the pipe 2, flows from the upper section of the pipe 2a inside the measuring device 1, where, in correspondence with the divergent section 3a, following the divergent profile in the direction of the flow of the upper ogive 5a, undergoes a radial deviation. The specific geometry of the system is such that the fluid threads, moving towards the annular support 4, are equally distributed between all the non-sampling channels 6a and sampling channels 6b inside the vertical sections 6a1 and 6b1. The portion of fluid threads 9, which passes inside the non-sampling channels 6a, is straightened in the first section 6a1 due to the flow restriction 26 and, in correspondence with the second section of non-sampling channel 6a2, undergoes a deviation in a convergent radial direction which accompanies it in its flow inside the convergent section 3c. Following the convergent profile in the direction of the flow of the lower ogive 5b, the portion of fluid threads 9 is sent to the lower section of the pipe 2b. The portion of fluid threads 10, which passes inside the sampling channels 6b, is straightened in the first section 6b1 due to the flow restriction 26 and, in correspondence with the second section of the non-sampling channel 6b2, undergoes a deviation in a divergent radial direction which accompanies it in its flow towards the outer perimeter of the sampling device 1 inside the pipe 16.

With reference to FIG. 1, a sampling is isokinetic when it is characterized by a zero pressure difference between the fluid removed and the non-removed fluid, downstream of the sampling, which, for the system under examination is verified when the ΔP registered by the differential pressure measurer 12 is zero. If the data processing system 31 receives a differential pressure value from the differential pressure measuring device 12 which is not zero, it sends an operative signal which acts on the regulation of the valve 23 causing a variation in the flow-rate of the sampled fluid 10 which is such as to annul the differential pressure at the measuring device 12. Alternatively, this regulation can be effected manually.

Furthermore, if the flow-rate of liquid separated from the fluid mixture is not revealed with the measuring device 19, the data processing system 31 allows flow-rate measurements to be effected discontinuously, by acting on the closing of the valve 20. The discontinuous measurement of the liquid flow-rate is effected by determining the time necessary for filling a known volume included between two prefixed heights using the level indicator 21 situated on the separator 15.

The multiphase flow measurement system according to the present invention, exclusively using measurers of the known type and a compact isokinetic sampling section, has a simple structure and volume with a reduced encumbrance. In addition, it does not require any type of self-calibration.

It should be pointed out that the percentage of sampled fluid varies, by varying the ratio between the total number of channels n and the number of sampling channels m. The variability range of the fluid fraction removed and therefore the m/n ratio, falls within a range of 5 to 20% of the overall flow.

It should be pointed out that the terms "upper" and "lower", "high" and "low", used in the present description and claims, refer to the vertical orientation of the axis of the section of pipe 2 in which the tubular body 3 is coaxially inserted and are equivalent to the terms "upstream" and "downstream" in the case of a generic orientation of said axis.

The invention claimed is:

1. An apparatus for measuring the liquid and gas flow-rates $Q_L$ and $Q_G$ in a multiphase stream which flows in a pipe, comprising:
a measuring unit which coaxially intercepts two portions of the pipe, including:
a) an isokinetic sampling device for the sampling of a portion of said multiphase stream, suitable for separating said multiphase stream into a sampled fraction and a non-sampled fraction, said device comprising a tubular body coaxial to the portions of said pipe and a distributing body positioned inside said tubular body suitable for generating a uniform radial distribution of the flow of said multiphase stream entering into n channels, of which m are sampling channels, annularly arranged on said distributing body which guarantee that the sampled fraction will have properties, in particular fractions by volume of the present phases and rates, almost identical to those of the non-sampled fraction;
b) differential pressure measuring means between said sampled fraction and said non-sampled fraction situated downstream of the sampling;
c) a flow restriction, having a reduced passage section with respect to the section of the pipe, situated downstream of said isokinetic sampling device equipped with a differential pressure measuring means associated with the flow restriction;
separation means for separating the liquid and gaseous phase of said sampled fraction in said isokinetic sampling apparatus;
measuring means at the outlet of said separation means for producing measuring signals of the liquid and gas flow-rates in the sampled fraction;
regulation means, installed after the remixing of the liquid and gaseous fractions leaving the separator for controlling the sampled flow-rate by means of said isokinetic sampling device;
data processing means suitable for receiving and processing the signals coming from the pressure indicators and flow-rate measurers and sending operative signals to said regulation means for varying the flow-rate of the sampled fraction in said sampling device.

2. The measuring apparatus according to claim 1, wherein said tubular body of said isokinetic sampling device comprises a divergent section, a cylindrical section and a convergent section, coaxially and sequentially connected one to another, said divergent section extending between the upper pipe section and the cylindrical section, said convergent section extending between the cylindrical section and the lower piping section.

3. The measuring apparatus according to claim 2, wherein said divergent section has a truncated-conical form with a smaller diameter equal to the diameter of the upper section of piping and a larger diameter equal to the diameter of the tubular section, said convergent section having a truncated-conical form with a larger diameter equal to the diameter of the tubular section and a smaller diameter equal to the diameter of the lower section of piping.

4. The measuring apparatus according to claim 1 wherein said distribution body comprises an annular support axially fixed inside said cylindrical section of the tubular body and a rotation solid positioned coaxially inside said annular support and comprising two substantially conical ogives extending axially above and below said annular support respectively inside the upper half of the cylindrical section and the divergent section and inside the lower half of the cylindrical section and the convergent section of the tubular body.

5. The measuring apparatus according to claim 4, wherein said two ogives have the respective tips facing said upper section and lower section respectively, of said pipe.

6. The measuring apparatus according to claim 4, wherein said n channels, of which m are sampling channels, are situated along said annular support equidistanced angularly and equi-distributed and having an equal section.

7. The measuring apparatus according to claim 6, wherein said non-sampling channels and said sampling channels comprise a first section of channel parallel to the axis of said tubular body and a second section of channel which is tilted towards the inside of said tubular body for said non-sampling channels and towards the outside for said sampling channels.

8. The measuring apparatus according to claim 7, wherein the tilted sections of said non-sampling channels have the same tilting angle as the tilted sections of said sampling channels and opposite directions.

9. The measuring apparatus according to claim 8, wherein said tilting angle ranges from 10 to 30°.

10. The measuring apparatus according to claim 7, wherein said differential pressure measuring means have pressure measuring points in correspondence with said first sections of said non-sampling channel.

11. The measuring apparatus according to claim 10, wherein said pressure measuring points are situated at a distance from the inlet not greater than the double of the diameter of said channels.

12. The measuring apparatus according to claim 7, wherein the length of said first sections of channels is equal to 8-10 times the diameter of said sampling channels.

13. The measuring apparatus according to claim 1, wherein a ratio between an area of a flow section of the sampled fraction $A_2$ and an area of the flow section of the total multiphase mixture $A_1$ is equal to a ratio between said number m of sampling channels and said total number n of channels.

14. The measuring apparatus according to claim 7, wherein said flow restriction is situated at a distance from an inlet of said first sections of channels equal to 4-5 times their diameter and is such to reduce a passage section of the channel by 20-30%.

15. The measuring apparatus according to claim 13, wherein said ratio between the areas $A_1$ with respect to $A_2$ is variable within a range of 5 to 20% by varying the ratio between said total number of channels n and said number of sampling channels m.

16. The measuring apparatus according to claim 1, wherein opening/closing means are provided on a liquid fraction leaving said separation means to effect discontinuous measurements of a liquid flow-rate through a level measurer associated with said separation means.

17. A method for measuring the liquid $Q_L$ and gaseous $Q_G$ flow-rates in a multiphase stream with a flow-rate Q which flows inside a pipe, comprising:
collecting a portion of flow-rate q of said multiphase stream from a section of area $A_1$, in which substantially isokinetic conditions are verified, by means of an isokinetic sampling device defining a sampling section $A_2$, $A_2$ being a fraction of $A_1$;
separating said portion of sampled stream into single liquid and gaseous phases components;
measuring the flow-rates of the liquid phases $q_L$ and gaseous $q_G$ components of said portion of sampled stream;
said method being characterized in that for the sampling of said portion of the multiphase stream, the latter is distributed, according to a uniform radial distribution of the flow, into n streams, of which m are sampling streams having a rate and volumetric fractions of the phases present almost identical to those of the non-sampled streams, said flow distribution being effected in n channels arranged annularly where the m sampling channels have an overall passage section equal to $A_2$; and in that it also comprises the following phases:

obtaining a differential pressure signal downstream of said sampling between the sampled fraction and non-sampled fraction;

varying the flow-rate of said sampled portion of the overall stream so that said differential pressure signal is equal to zero;

calculating, under isokinetic conditions, the total flow-rate of the multiphase stream as the sum of the flow-rates of the gaseous fraction $Q_G$ and liquid fraction $Q_L$ once the flow-rates of the gas phase $q_G$ and liquid phase a in said sampled portion of the overall stream, have been measured, on the basis of the relations $$Q_G = A_1/A_2 q_G = n/m q_G$$

and $$Q_L = A_1/A_2 q_L = n/m q_L.$$

18. The measuring method according to claim 17, wherein the uniform radial distribution of the flow is obtained by radially deviating the multiphase stream along a divergent rotation surface around the flow axis, said n channels being arranged annularly, equidistanced around the end having a greater diameter of said divergent surface, said n channels having a portion parallel to said flow axis and a portion tilted towards said axis for n–m non-sampling channels and tilted in the opposite direction for n sampling channels.

19. The measuring method according to claim 17 or 18, wherein the non-sampled portion of said multiphase stream, leaving said n–m non-sampling channels, is radially deviated along a convergent rotation surface around the flow axis before being re-introduced into said pipe.

* * * * *